US007181284B2

(12) United States Patent
Burnes et al.

(10) Patent No.: US 7,181,284 B2
(45) Date of Patent: *Feb. 20, 2007

(54) APPARATUS AND METHODS OF ENERGY EFFICIENT, ATRIAL-BASED BI-VENTRICULAR FUSION-PACING

(75) Inventors: John E. Burnes, Andover, MN (US); Thomas J. Mullen, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 42 days.

This patent is subject to a terminal disclaimer.

(21) Appl. No.: 10/803,570

(22) Filed: Mar. 17, 2004

(65) Prior Publication Data
US 2005/0209648 A1 Sep. 22, 2005

(51) Int. Cl.
*A61N 1/36* (2006.01)
(52) U.S. Cl. ...................................... 607/25
(58) Field of Classification Search .............. 607/4, 607/5, 9, 115–123, 17–18, 25
See application file for complete search history.

(56) References Cited

U.S. PATENT DOCUMENTS

| 4,428,378 | A | | 1/1984 | Anderson et al. | |
|---|---|---|---|---|---|
| 5,052,388 | A | | 10/1991 | Sivula et al. | |
| 5,534,016 | A | | 7/1996 | Boute | |
| 5,626,620 | A | | 5/1997 | Kieval et al. | |
| 5,658,320 | A | | 8/1997 | Betzold et al. | |
| 5,741,308 | A | * | 4/1998 | Sholder | 607/9 |
| 5,759,196 | A | | 6/1998 | Hess et al. | |
| 5,814,083 | A | | 9/1998 | Hess et al. | |
| 5,935,160 | A | * | 8/1999 | Auricchio et al. | 607/122 |
| 6,038,474 | A | | 3/2000 | Zhu et al. | |
| 6,275,731 | B1 | | 8/2001 | Zhu et al. | |
| 6,370,427 | B1 | * | 4/2002 | Alt et al. | 607/4 |
| 6,473,649 | B1 | | 10/2002 | Gryzwa et al. | |
| 6,477,415 | B1 | * | 11/2002 | Yerich et al. | 607/9 |
| 6,501,988 | B2 | | 12/2002 | Kramer et al. | |

(Continued)

FOREIGN PATENT DOCUMENTS

WO WO/03/037427 5/2003

OTHER PUBLICATIONS

Article entitled "Left Ventricular and Biventricular Pacing in Congestive Heart Failure," from *Mayo Foundation for Medical Education and Research*, 2001; 76:803-812.

(Continued)

*Primary Examiner*—Robert E. Pezzuto
*Assistant Examiner*—Jessica L. Reidel
(74) *Attorney, Agent, or Firm*—Girma Wolde-Michael; Paul H. McDowall

(57) ABSTRACT

The bi-ventricular implantable pulse generator described and depicted herein enables hemodynamic efficiencies for patients suffering from intraventricular conduction delays or conduction blockage. The pulse generator effectively overcomes such conduction delay or block (e.g., left bundle branch block, "LBBB," or right bundle branch block, "RBBB") by delivering a novel form of cardiac resynchronization therapy (CRT). Specifically, a single ventricular pre-excitation pacing stimulus is triggered from an atrial event (e.g., intrinsic or evoked depolarization). The triggering event may emanate from the right atrium (RA) or the left atrium (LA). A single ventricular pre-excitation pacing stimulus is delivered prior to the intrinsic depolarization of the other ventricle and thus promotes intraventricular electromechanical synchrony during CRT delivery.

51 Claims, 6 Drawing Sheets

U.S. PATENT DOCUMENTS

| | | |
|---|---|---|
| 6,553,258 B2 | 4/2003 | Stahmann et al. |
| 6,871,096 B2* | 3/2005 | Hill .............................. 607/25 |
| 2003/0014084 A1* | 1/2003 | VanHout ........................ 607/9 |
| 2003/0028222 A1 | 2/2003 | Stahmann |
| 2003/0083700 A1 | 5/2003 | Hill |
| 2005/0055058 A1* | 3/2005 | Mower .......................... 607/9 |
| 2005/0137630 A1* | 6/2005 | Ding et al. .................... 607/9 |
| 2005/0209649 A1 | 9/2005 | Ferek-petric |
| 2005/0209650 A1 | 9/2005 | VanGelder et al. |

OTHER PUBLICATIONS

Article entitled "Endocardial versus epicardial electrical synchrony during LV free-wall pacing," from *Am. J. Physical Circ, Physiol*, Jul. 10, 2003; pp. H1864-70.

Presentation entitled "Selection of Patients and Optimization of Pump Function in Resynchronization Therapy Based on Interventricular Asynchrony," by Xander, et al., Nov. 12, 2003.

\* cited by examiner

APPARATUS AND METHODS OF ENERGY EFFICIENT, ATRIAL-BASED BI-VENTRICULAR FUSION-PACING

CROSS REFERENCE TO RELATED APPLICATIONS

This patent application relates to a non-provisional U.S. patent application by Hill, namely Ser. No. 10/000,474 filed 26 Oct. 2001 and entitled, "System and Method for Bi-Ventricular Fusion-pacing" now U.S. Pat. No. 6,871,096; a non-provisional U.S. patent application by Pilmeyer and van Gelder; namely Ser. No. 10/802,419 filed 17 Mar. 2004, and entitled, "APPARATUS AND METHODS FOR 'LEPARS' INTERVAL-BASED FUSION-PACING;" and a non-provisional U.S. patent application by B. Ferek-Petric; namely Ser. No. 10/802,953 filed 17 Mar. 2004, and entitled, "MECHANICAL SENSING SYSTEM FOR CARDIAC PACING AND/OR FOR CARDIAC RESYNCHRONIZATION THERAPY," now abandon the entire contents of each is hereby incorporated by reference herein.

FIELD OF THE INVENTION

The invention pertains to cardiac resynchronization pacing systems. In particular, the invention relates to apparatus and methods for automatically adjusting an AV interval during single ventricle pacing to efficiently deliver fusion-based cardiac resynchronization therapy (CRT) via ventricular pre-excitation. The invention can be configured to compensate for cardiac conduction defects such as left or right bundle branch block (LBBB, RBBB, respectively).

BACKGROUND OF THE INVENTION

In the above-referenced patent application to Hill, Hill discloses that in certain patients exhibiting symptoms resulting from congestive heart failure (CHF), cardiac output is enhanced by timing the delivery of an left ventricular (LV) pacing pulse such that evoked depolarization of the LV is effected in fusion with the intrinsic depolarization of the right ventricle (RV). The fusion depolarization enhances stroke volume in such hearts where the RV depolarizes first due to intact atrio-ventricular (AV) conduction of a preceding intrinsic or evoked atrial depolarization wave front, but wherein the AV conducted depolarization of the LV is unduly delayed. The fusion depolarization of the LV is attained by timing the delivery of the LV pace (LVp) pulse to follow the intrinsic depolarization of the RV but to precede the intrinsic depolarization of the LV. Specifically, an RV pace (RVp) pulse is not delivered due to the inhibition of the RVp event upon the sensing of RV depolarization (RVs), allowing natural propagation of the wave front and depolarization of the intraventricular septum, while an LVp pulse is delivered in fusion with the RV depolarization.

However, due to a number of factors (e.g., the amount of time required for appropriate signal processing, confounding conduction delays or conduction blockage of a patient, diverse electrode placement locations, and the like) for a variety of patients the system described may not always effectively delivery CRT.

A need therefore exists in the art to efficiently and chronically delivery CRT to patients suffering from various cardiac conduction abnormalities who might not otherwise receive the benefits of CRT therapy.

SUMMARY

For some patients suffering from heart failure and intra-ventricular conduction delays (e.g., LBBB, RBBB) the delivery of CRT may be effected with a single ventricular pacing stimulus by pre-exciting the conduction-delayed ventricle. Such a stimulus must be properly timed relative to intrinsic depolarization of the other, non-delayed ventricle. This phenomenon is referred to herein as a new, efficient form of "fusion-pacing" since ventricular activation from a pacing stimulus fuses or merges with ventricular activation from intrinsic conduction. When the ventricular pacing stimulus is properly timed a desired ventricular resynchronization results with a minimum of pacing energy, thereby extending the operating life of an implantable pulse generator (e.g., an implantable cardioverter-defibrillator, pacemaker, and the like). Moreover, in some cases a more effective or physiologic form of CRT delivery can be achieved since the system and methods herein utilize a portion of intrinsic activation, which can be superior to an entirely evoked (i.e., paced) form of CRT.

The challenge in such a system is determining the appropriate moment to delivery the single ventricular pacing stimulus, especially since such timing can be expected to vary with the timing dependent on the physiologic status of the patient (e.g., exercise, medications etc). In addition to the foregoing, the inventors hereof have discovered a novel means of appropriately timing the ventricular pacing stimulus based on evaluation of at least one prior cardiac event. The inventors have discovered that for some heart failure patients suffering from intraventricular conduction delays such as left bundle branch block (LBBB) or right bundle branch block (RBBB), efficient delivery of CRT can be achieved. According to the present invention, the triggering of a single ventricular pacing stimulus occurs upon expiration of an AV interval timed from at least one prior atrial event (paced or sensed; represented herein as "$A_{p/s}$") and determined from at least one prior $A_{p/s}$, that resulted in a sensed ventricular event (Vs). The triggering event, $A_{p/s}$, can emanate from the right atrium (RA) or the left atrium (LA) and the single ventricular pacing stimulus is timed to pre-excite one ventricle so that intra-ventricular mechanical synchrony results. The mechanical synchrony results from the fusing of the two ventricular depolarization wavefronts (i.e., one paced and the other intrinsically-conducted).

According to the present invention, delivery of a single ventricular pacing stimulus occurs upon expiration of a fusion-AV or, herein referred to as the pre-excitation interval ("PEI"). One way to express this relationship defines the PEI as being based on an intrinsic AV interval or intervals from an immediately prior cardiac cycle or cycles ($AV_{n-1}$ or $AV_{n-1}$, $AV_{n-2}$, $AV_{n-3}$, etc.). Thus, in this "form" of the invention PEI can be expressed as $PEI=AV_{n-1}-V_{pei}$, wherein the AV interval represents the interval from an A-event ($A_{p/s}$) to the resulting intrinsic depolarization of a ventricle (for a prior cardiac cycle) and the value of PEI equals the desired amount of pre-excitation needed to effect ventricular fusion (expressed in ms). For a patient with LBBB conduction status (for a current cardiac cycle "n") the above formula can be expressed as: $A\text{-}LVp_n = A\text{-}RV_{n-1} - LV_{pei}$ and for a patient suffering from RBBB conduction status the formula reduces to: $A\text{-}RVp_n = A\text{-}LV_{n-1} - RV_{pei}$.

As noted above, the timing of the single ventricular pacing stimulus is an important parameter when delivering therapy according to the present invention. While a single, immediately prior atrial event ($A_{p/s}$) to a RV or an LV sensed depolarization can be utilized to set the PEI and derive the timing for delivering pacing stimulus (i.e., A-RV$_{n-1}$ or A-LV$_{n-1}$) more than a single prior sensed AV interval, a prior PEI, a plurality of prior sensed AV intervals or prior PEIs can be utilized (e.g., mathematically calculated values such as a temporal derived value, a mean value, an averaged value, a median value and the like). Also, a time-weighted value of the foregoing can be employed wherein the most recent values receive additional weight. Alternatively, the PEI can be based upon heart rate (HR), a derived value combining HR with an activity sensor input, P-wave to P-wave timing, R-wave to R-wave timing and the like. Again, these values may be time-weighted in favor of the most, or more, recent events. Of course, other predictive algorithms could be used which would account for variability, slope or trend in AV interval timing and thereby predict AV characteristics.

In another embodiment of the present invention, a data set optionally configured as a look-up-table (LUT) correlating HR, activity sensor signal input, and/or discrete physiologic cardiac timing intervals can be used to set an appropriate PEI. If a mathematical derivation of HR is used to set the PEI, the data set or LUT can comprise at least two data sets or LUTs, one for stable or relatively stable HR, and another for various rate-of-change of the HR to more accurately reflect a physiologic PEI. More generally, multiple LUTs may be utilized that correlate to one or more physiologic parameters (e.g., contains PEIs for RV-only pacing, for LV-only pacing, for sensed atrial events, for paced atrial events, or PEIs derived at least in part as a function of HR). In the latter embodiment, the present invention can be quickly reconfigured to adapt to paroxysmal conduction blockage episodes, or so-called conduction alternans (e.g., wherein cardiac conduction appears to mimic LBBB for some cardiac cycles and RBBB for others). In one refinement of the foregoing, the A-RVs or A-LVs interval, or series of intervals, used to calculate the timing of the pre-excitation ventricular stimulation can be divided into a pair of intervals, depending on whether the A event was a sensed, intrinsic atrial depolarization (As) event or an atrial pacing event (Ap).

Among other aspects of the present invention provides an energy-efficient manner of providing single ventricle, pre-excitation fusion-pacing therapy. Heretofore, such pre-excitation was not possible because in the prior art, the fusion-pacing stimulus was triggered by a sensed event in the opposite chamber. In the case of fusion-pacing delivered to the LV, a pacing stimulus is provided via at least one electrode disposed in electrical communication with a portion of the LV (e.g., an electrode deployed into a portion of the coronary sinus (CS), great vein, and branches thereof or epicardially). Since an evoked depolarization from such electrode placement excites the myocardium from the opposite side of the ventricular wall (versus normal intrinsic cardiac excitation), the LV may need to be excited before an intrinsic sense (RVs) occurs for the same cycle to achieve optimal performance. In one aspect, the present invention allows for dual chamber (atrial and ventricular) CRT delivery which can be employed with a simple pair of electrical medical leads. The first lead operatively couples to an atrial chamber and the second lead operatively couples to a slow- or late-depolarizing ventricular chamber, such as the LV. In this form of the invention, the lead disposed in communication with the ventricular chamber can be used for "far field" sensing of intrinsic ventricular depolarizations. Optionally, a third lead may be used to sense intrinsic activation in the opposite ventricular chamber or other part of the same chamber.

A variety of locations for the atrial lead can be used successfully in practicing the methods of the present invention. For example, electrical communication (e.g., pacing and sensing an atrial chamber) with the RA can utilize an epicardial or endocardial location and any appropriate sensing vector. Similarly, the intrinsic depolarization of the ventricle can utilize any known sensing vector (e.g., tip-to-ring, coil-to-can, coil-to-coil, etc.). An endocardial location may include the common RA pacing site of the RA appendage although RA septal or other locations are acceptable. An electrode operatively coupled to the LA may also be used, including such locations as the CS and portions distal to the os of the CS, as well as the inter-atrial septal wall, among others. The locations at which the RV and LV leads couple with the myocardium can vary within each chamber, and depending on whether the patient has an RBBB or an LBBB will influence how this therapy is implemented to achieve intraventricular synchrony within the chamber where the bundle branch block occurs. In the case of LBBB, a lead operatively coupled to the RV is used to sense intrinsic depolarizations for determining the timing needed for the operative pacing interval (e.g., A-LVp interval). This lead may be used in a variety of endocardial or epicardial locations and more than one electrical lead and/or more than one pair of pace/sense electrodes may be operatively coupled to a single cardiac chamber. With respect to endocardial locations, RV apical, RV outflow tract (RVOT), RV septal, RV free wall and the like will provide benefits according to the present invention. In the case of RBBB, a lead can be operatively positioned in or near the epicardium or endocardium of the LV for sensing intrinsic depolarizations used to determine the operative pacing timing.

For the purposes of this disclosure, an implementation for a patient with a LBBB will be depicted and described; however, this exemplary depiction is no way limiting for example, among others, that an RBBB or nonspecific bundle branch block implementation can be practiced. For example, the RBBB condition can be accommodated by simply monitoring LV conduction patterns by operatively coupling a sensing electrode to the LV and a pre-excitation pacing electrode to the RV (e.g., apex of the RV, RVOT, free wall, etc.). In addition to the number of pace/sense electrodes employed, a variety of unipolar or bipolar sensing vectors between electrodes may be implemented, including tip-to-ring, coil-to-can, coil-to-coil, and the like.

In terms of timing of the ventricular pacing stimulus, a measurement of at least one prior A$_{p/s}$-RVs interval (from a paced or intrinsic atrial depolarization) provides a beginning point for determining an appropriate single-chamber pacing interval (e.g., A$_{p/s}$-LVp interval) that produces ventricular fusion. Furthermore, this algorithm can be expanded so that multiple A-RVs intervals are measured and used to calculate, or predict, a subsequent A$_{p/s}$-LVp. As mentioned hereinabove, time-weighted values of previous A-RVs may optionally be employed to finalize an operational A$_{p/s}$-LVp value for the current beat. During delivery of a fusion-pacing therapy according to the present invention, the actual timing of LVp events and RVs events can be monitored to confirm that the actual operating PEI equals (or is adequately close to) the desired or programmed LV$_{pei}$.

Further addition, one or more mechanical, acoustic and/or activity sensors may be coupled to the heart and used to confirm that a desired amount of bi-ventricular synchrony results from the delivered therapy. Some representative mechanical sensors for this purpose include fluid pressure sensors or acceleration sensors and the like. The mechanical sensors operatively couple to the heart (e.g., LV lateral free-wall, RV septal wall, epicardial RV locations, etc.). Output signals from such sensors may be used to modify the timing of the fusion-pacing stimulus, especially during episodes such as a rapidly changing HR.

In addition to the therapy delivery aspects of the present invention, a limited number of therapy delivery guidance or security options may be used to determine if the pre-excitation fusion-pacing therapy ought to be modified, initiated or discontinued. For example, in the event a transient conduction anomaly interrupting AV conduction is detected a pacing modality switch to a double or triple chamber pacing modality could be implemented. In the event that the pre-excitation interval is shortened so much that a pacing stimulus occurs during the refractory period of the ventricle—thereby causing loss of capture or potential for inducing an arrhythmia—fusion-pacing could cease or the operative pacing interval could be lengthened (e.g., up to an amount approximately equal to the A-Vs interval of the other ventricle). If one of the sensors indicates increasing ventricular asynchrony or decreasing hemodynamic response to the therapy, the atrial-based fusion-pacing therapy could be modified or could cease. One such modification could be an adjustment of the amount of pre-excitation based on output from these sensors. Furthermore, from time-to-time the atrial-based fusion-pacing therapy could be suspended while cardiac activity is monitored so that any change in normal sinus rhythm, or improvement in ventricular synchrony (e.g., desirable so-called "reverse remodeling") can be accommodated. In the event that ventricular synchrony and conduction improves markedly, or that the suspension of CRT results in improved hemodynamics, a pacing mode switch from CRT to an atrial-based pacing mode such as AAI, ADI, AAI/R, ADI/R and the like may be implemented thereby providing a highly efficient and physiologic pacing regime for the patient. Thereafter, in the event that conduction anomalies cause ventricular asynchrony and resultant hemodynamic compromise or heart failure decompensation, another pacing mode switch can be implemented to resume an atrial-based fusion-pacing mode according to the present invention.

The foregoing and other aspects and features of the present invention will be more readily understood from the following detailed description of the embodiments thereof, when considered in conjunction with the drawings, in which like reference numerals indicate similar structures throughout the several views.

DETAILED DESCRIPTION OF THE ILLUSTRATED EMBODIMENTS

In the following detailed description, references are made to illustrative embodiments for carrying out an energy efficient, single-pacing stimulus, ventricular pre-excitation pacing mode according to the present invention. It is understood that other embodiments may be utilized without departing from the scope of the invention. For example, the invention is disclosed in detail herein in the context of an intrinsically-based or AV sequential (evoked) uni-ventricular pacing system with dual ventricular sensing that operates in an atrial tracking, demand and/or triggered pacing modes. The present invention provides an efficient pacing modality for restoring electromechanical ventricular synchrony based upon either atrial-paced or atrial-sensed events particularly for patients with some degree of either chronic, acute or paroxysmal ventricular conduction block (e.g., intraventricular, LBBB, RBBB). Cardiac pacing apparatus, according to the invention, are programmable to optionally operate as a dual- or triple-chamber pacing system having an AV synchronous operating mode for restoring upper and lower heart chamber synchronization and right and left atrial and/or ventricular chamber depolarization synchrony. A system according to the invention efficiently provides cardiac resynchronization therapy (CRT) with a single ventricular stimulus per cardiac cycle. In one embodiment, the inventive pacing system operates in a V2DD or V2DD/R operating mode wherein intrinsic atrial events govern the timing of the A-V2$p$ pre-excitation interval. The foregoing novel pacing codes are derived from the well-known NASPE pacing codes wherein the "V2" is intended to indicate that pacing stimulus is delivered to the relatively late depolarizing ventricle (prior to activation of the relatively more early depolarizing ventricle, or "V1").

The present invention provides enhanced hemodynamic performance for patients having intact AV nodal conduction but that nevertheless suffer from various forms of heart failure, ventricular dysfunctions and/or ventricular conduction abnormalities. Pacing systems according to the present invention can also include rate responsive features and anti-tachyarrhythmia pacing and the like. In addition, a system according to the invention may include cardioversion and/or defibrillation therapy delivery.

Figure 1:
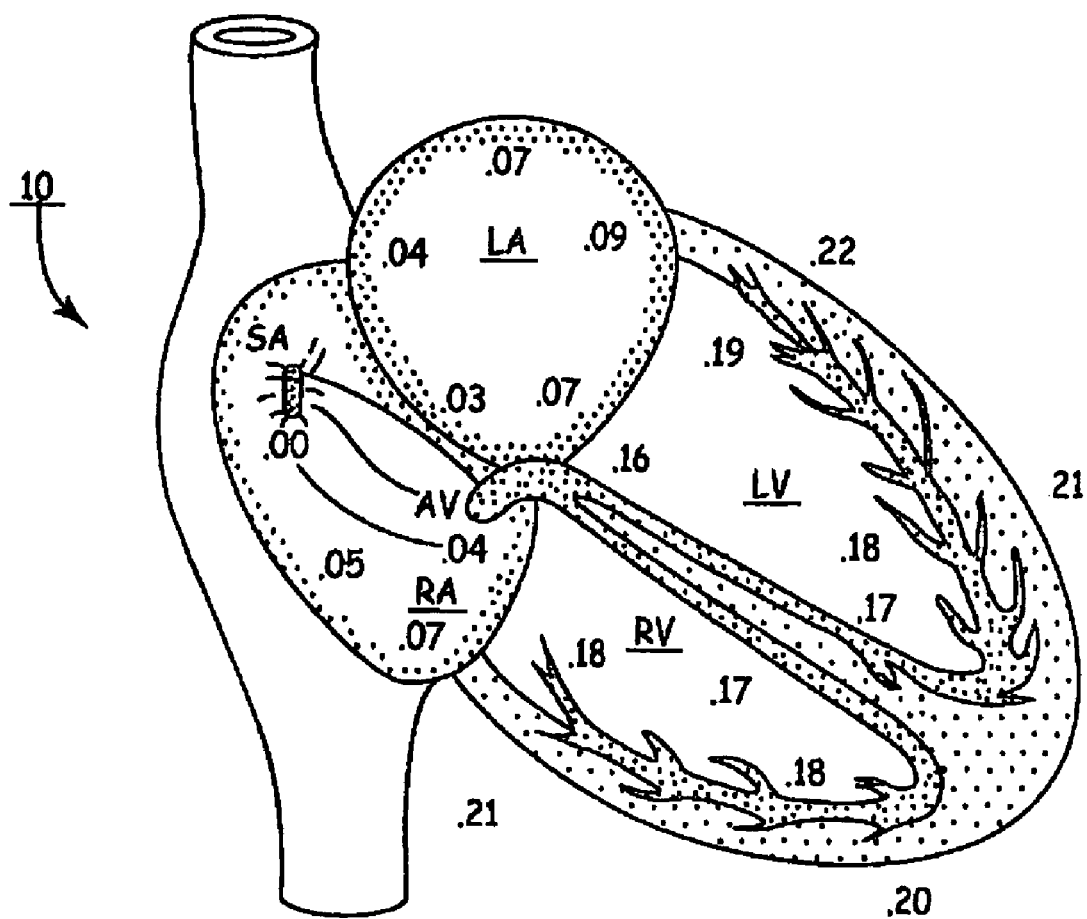
FIG. 1 is an illustration of transmission of a normal cardiac conduction system through which depolarization waves are propagated through the heart in a normal intrinsic electrical activation sequence.

In accordance with an aspect of the present invention, a method and apparatus is provided to mimic the normal depolarization-repolarization cardiac cycle sequence of FIG. 1 and restore cardiac intra- and/or inter-ventricular synchrony between the RV, septum, and LV that contributes to adequate cardiac output related to the synchronized electromechanical performance of the RV and LV. The foregoing and other advantages of the invention are realized through delivery of cardiac pacing stimulation to the later depolarizing ventricle (V2) that are timed to occur prior to a sensed depolarization in the other ventricle (V1). As a result of such timing, the V2 essentially is "pre-excited" so that the electromechanical performance of V1 and V2 merge into a "fusion event." The amount pre-excitation may be individually selectable or automatically determined. The amount of temporal pre-excitation can be linked to intrinsic propagation of cardiac excitation, which can change based on a number of factors. For example, physiologic conduction delay through the A-V node or through the His-Purkinje fibers, electrical conduction delay for sensing intracardiac events (from electrodes through threshold sensing circuitry of a medical device), electrical conduction delay for pacing therapy delivery circuitry, electromechanical delay associated with the delivery of a pace and the ensuing mechanical contraction, ischemic episodes temporarily tempering conduction pathways, myocardial infarction(s) zones, all can deleteriously impact cardiac conduction. Because the conduction status of a patient can vary over time and/or vary based on other factors such as heart rate, autonomic tone and metabolic status, the present invention provides a dynamically controllable single chamber resynchronization pacing modality. For example, based on one or more of several factors, a pre-excitation optimization routine (or sub-routine) can be triggered so that a desired amount of single-chamber fusion-based pacing ensues. Some of the factors include, (i) completion of a pre-set number of cardiac cycles, (ii) pre-set time limit, (iii) loss of capture of the paced ventricle (V2), and/or (iv) physiologic response triggers (e.g., systemic or intracardiac pressure fluctuation, heart rate excursion, metabolic demand increase, decrease in heart wall acceleration, intracardiac electrogram morphology or timing, etc.). The present invention provides a cardiac pacing system that can readily compensate for the particular implantation sites of the pace/sense electrode pair operatively coupled to the V2 chamber. When implemented in a triple-chamber embodiment, a pacing system according to the present invention can quickly mode switch in the event that a conduction defect appears in the non-pacing ventricle (V1) to either a true triple chamber bi-ventricular pacing mode (with or without CRT delivery) or to a dedicated double chamber pacing mode (e.g., DDD/R or VVI and the like).

Figure 2:
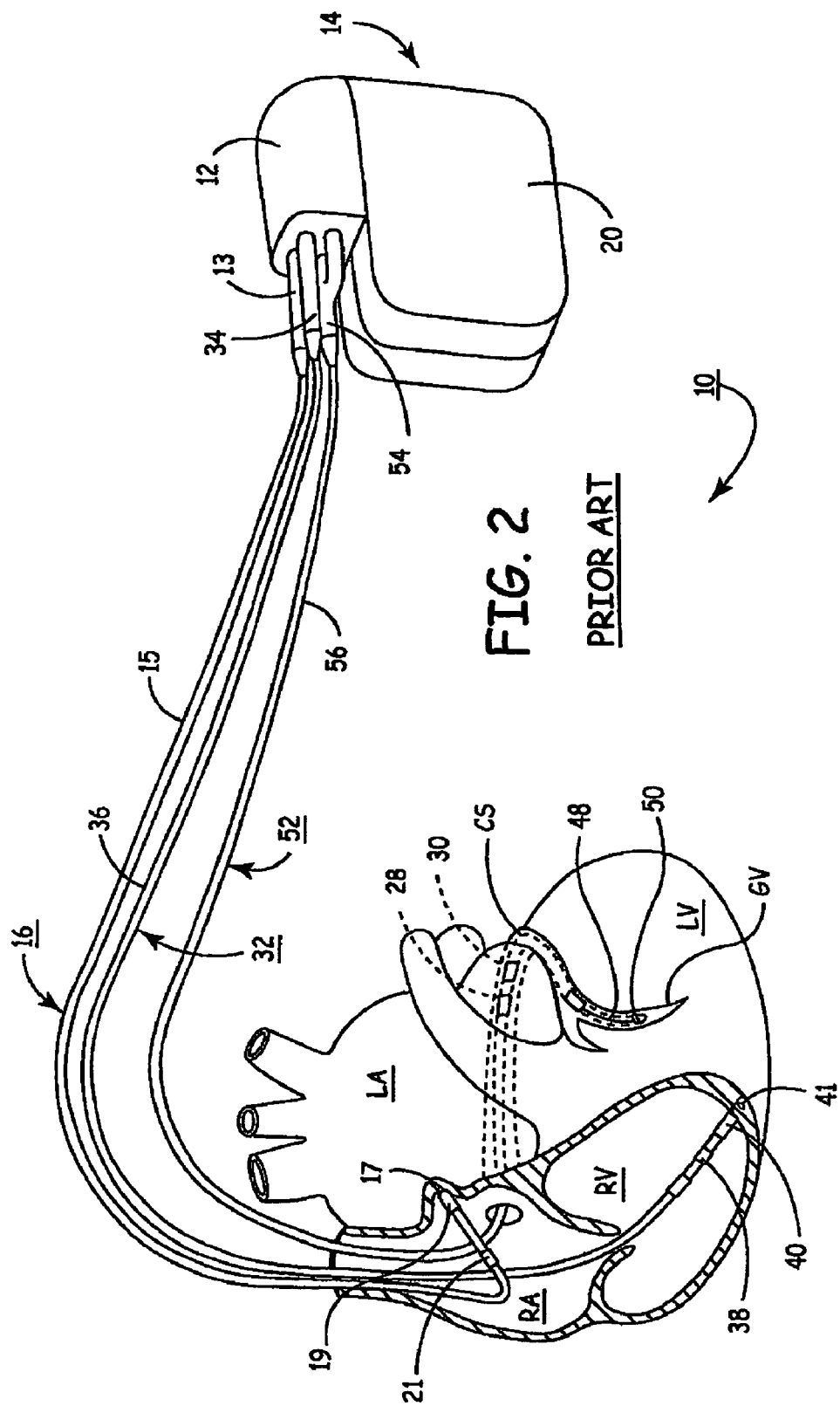
FIG. 2 is a schematic diagram depicting a three channel, atrial and bi-ventricular, pacing system for implementing the present invention.

FIG. 2 is a schematic representation of an implanted, triple-chamber cardiac pacemaker comprising a pacemaker IPG 14 and associated leads 16, 32 and 52 in which the present invention may be practiced. The pacemaker IPG 14 is implanted subcutaneously in a patient's body between the skin and the ribs. The three endocardial leads 16,32,52 operatively couple the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions, particularly sensing far field signals (e.g. far field R-waves). The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV. Also, as noted previously, multiple electrodes and/or leads may be deployed into operative communication with the relatively "late" depolarizing ventricle to pace at multiple sites with varying degrees of pre-excitation. In addition, mechanical and/or metabolic sensors can be deployed independent of, or in tandem with, one or more of the depicted leads. In the event that multiple pacing electrodes are operatively deployed, a PEI for all such electrodes may be individually calculated. That is, a slightly different amount of pre-excitation may be implemented for each discrete pacing location and said pre-excitation can thus be tuned for conduction anomalies (e.g., due to infarct or ischemia or the like).

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

Further referring to FIG. 2, a bipolar, endocardial coronary sinus (CS) lead 52 is passed through a vein and the RA chamber of the heart 10, into the coronary sinus and then inferiorly in a branching vessel of the great cardiac vein to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus, and into a coronary vein descending from the coronary sinus, such as the lateral or posteriolateral vein.

In a four chamber or channel embodiment, LV CS lead 52 bears proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching inferiorly from the great vein GV.

In this case, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrodes 21 and 38, respectively for pacing and sensing in the LA and LV, respectively.

Figure 3:
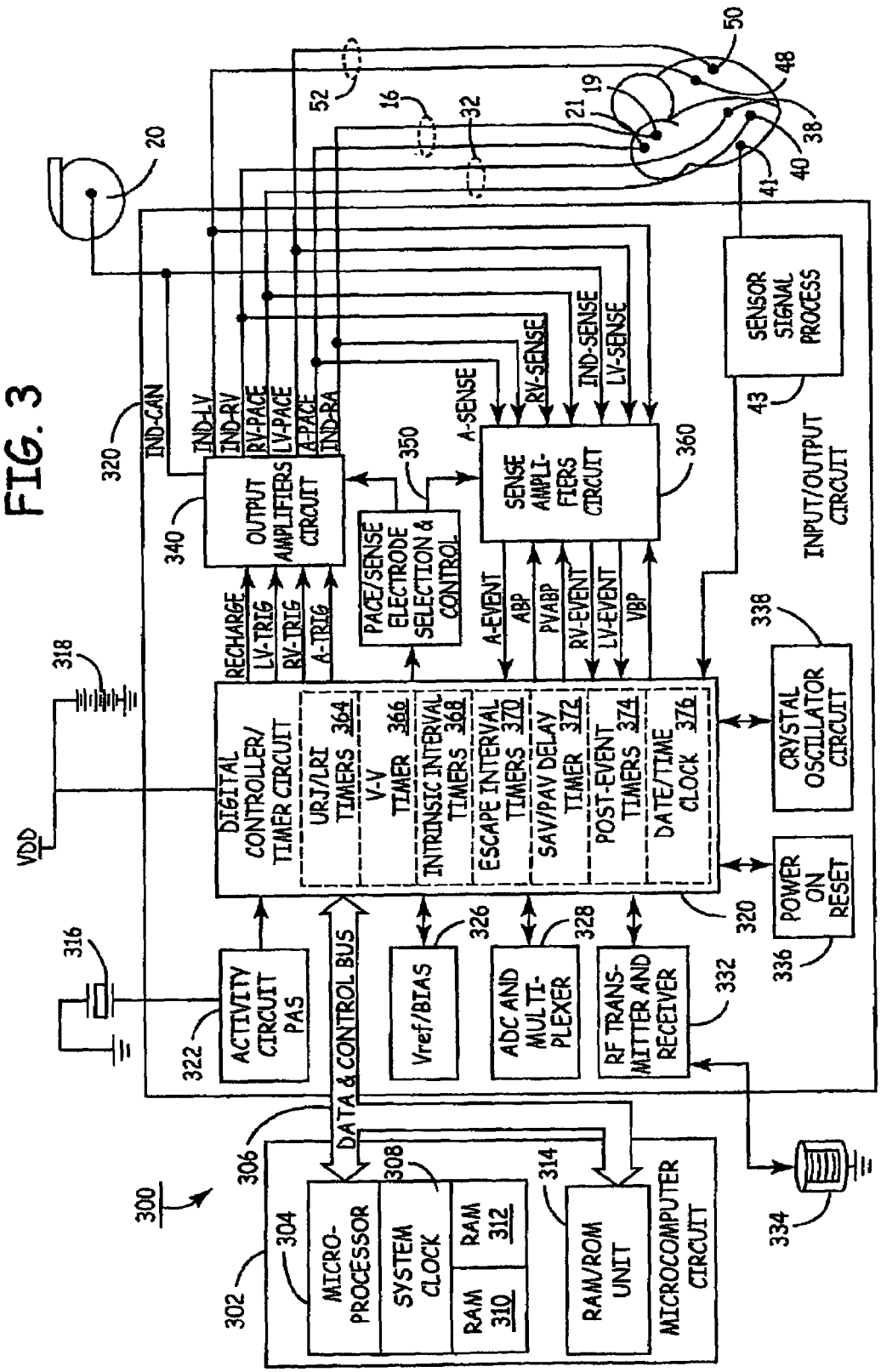
FIG. 3 is a simplified block diagram of one embodiment of IPG circuitry and associated leads employed in the system of FIG. 2 for providing three sensing channels and corresponding pacing channels that selectively functions in an energy efficient, single-pacing stimulus, ventricular pre-excitation pacing mode according to the present invention.

In this regard, FIG. 3 depicts bipolar RA lead 16, bipolar RV lead 32, and bipolar LV CS lead 52 without the LA CS pace/sense electrodes 28 and 30 coupled with an IPG circuit 300 having programmable modes and parameters of a bi-ventricular DDDR type known in the pacing art. In addition, at least one physiologic sensor 41 is depicted operatively coupled to a portion of myocardium and electrically coupled to a sensor signal processing circuit 43. In turn the sensor signal processing circuit 43 indirectly couples to the timing circuit 330 and via bus 306 to microcomputer circuitry 302. The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 322, the activity sensor circuit 322 as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 322 and provided to digital controller/timer circuit 330. Activity circuit 332 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 334 and an associated RF transceiver 332, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-TRIG, RV-TRIG, LV-TRIG signals generated by timers in digital timer/controller circuit 330 and A-EVENT, RV-EVENT, and LV-EVENT signals generated by sense amplifiers circuit 360, among others. The specific values of the intervals and delays timed out by digital controller/timer circuit 330 are controlled by the microcomputer circuit 302 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A—A, V-A, or V—V escape interval, as applicable. In addition, the microprocessor 304 may also serve to define variable AV delays and the uni-ventricular, pre-excitation pacing delay intervals (A-V2p) from the activity sensor data, metabolic sensor(s) and/or mechanical sensor(s).

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include URI/LRI timers 364, V—V delay timer 366, intrinsic interval timers 368 for timing elapsed V-EVENT to V-EVENT intervals or V-EVENT to A-EVENT intervals or the V—V conduction interval, escape interval timers 370 for timing A—A, V-A, and/or V—V pacing escape intervals, an AV delay interval timer 372 for timing the A-LVp delay (or A-RVp delay) from a preceding A-EVENT or A-TRIG, a post-ventricular timer 374 for timing post-ventricular time periods, and a date/time clock 376.

Figure 4:
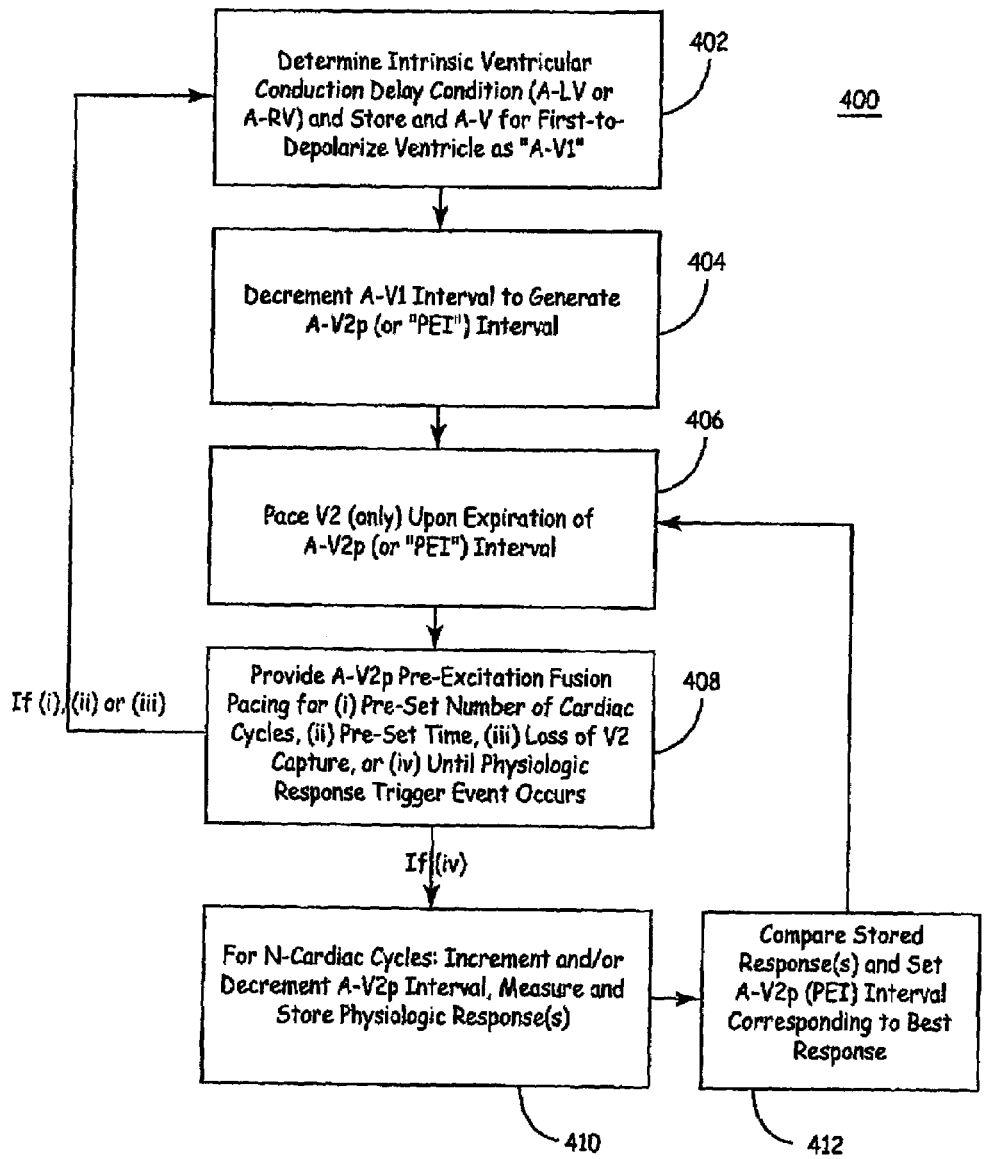
FIG. 4 illustrates an embodiment of the energy efficient, single-pacing stimulus, ventricular pre-excitation pacing mode according to the present invention.
Figure 5:
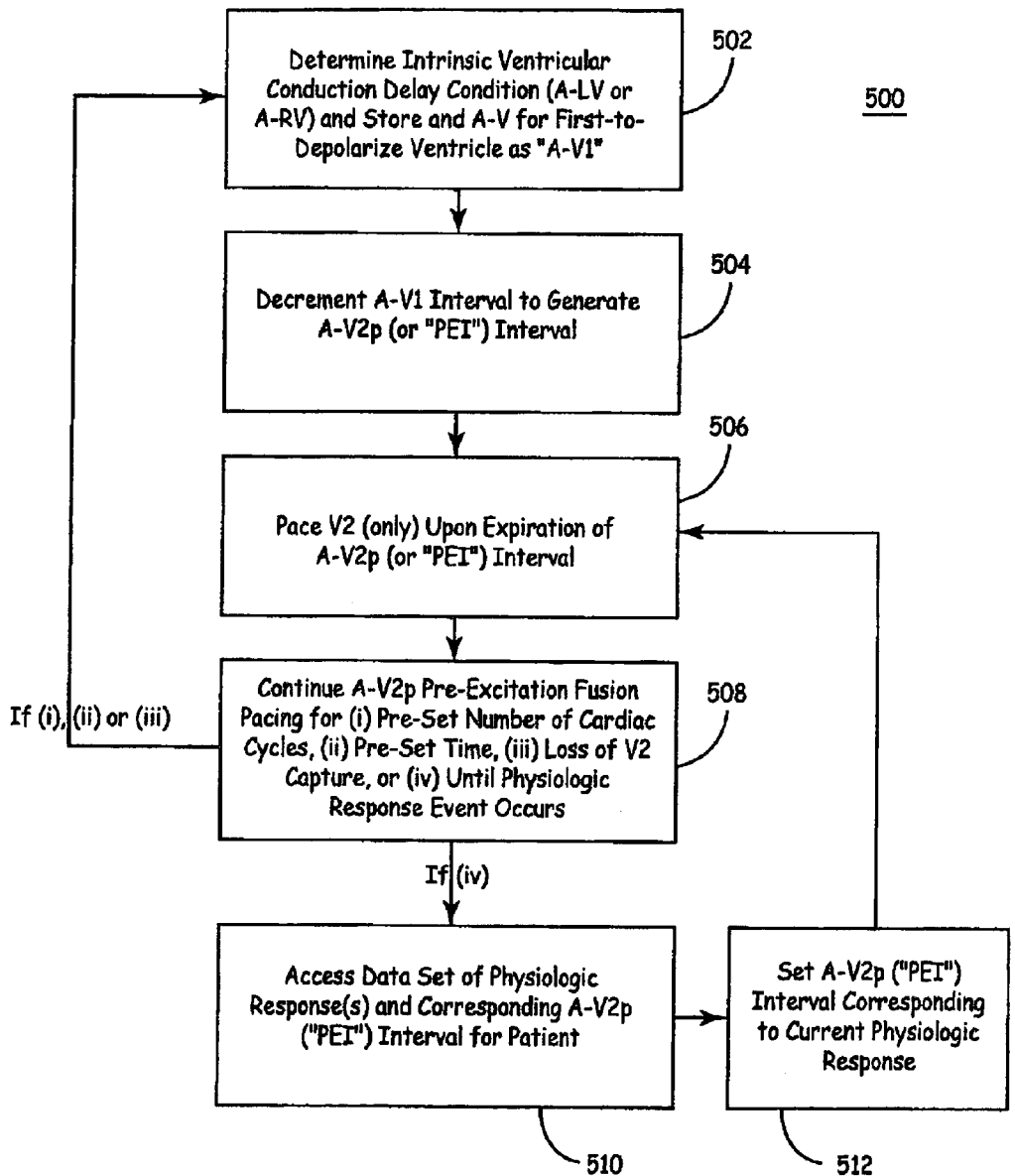
FIG. 5 illustrates an embodiment of the energy efficient, single-pacing stimulus, ventricular pre-excitation pacing mode according to the present invention.

According to the invention, the AV delay interval timer 372 is loaded with an appropriate delay interval for the V2 chamber (i.e., either an A-RVp delay or an A-LVp delay as determined by the flow chart depicted at FIG. 4 and FIG. 5)

to time-out starting from a preceding A-PACE or A-EVENT. The interval timer 372 times the PEI, and is based on one or more prior cardiac cycles (or from a data set empirically derived for a given patient) and does not depend on sensing of a depolarization in the other ventricle (i.e., V1) prior to delivery of the pace at V2 during pre-excitation fusion-based pacing therapy delivery according to the present invention.

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 304 also optionally calculates AV delays, post-ventricular time periods, and post-atrial time periods that vary with the sensor based escape interval established in response to the RCP(s) and/or with the intrinsic atrial rate.

The output amplifiers circuit 340 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 330 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 372 (or the V—V delay timer 366). Similarly, digital controller/timer circuit 330 generates an RA-TRIG signal that triggers output of an RA-PACE pulse (or an LA-TRIG signal that triggers output of an LA-PACE pulse, if provided) at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in contemporary cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pace pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in a LA-EVENT signal that is communicated to the digital controller/timer circuit 330. Ventricular depolarizations or R-waves in the RV-SENSE signal are sensed by a ventricular sense amplifier result in an RV-EVENT signal that is communicated to the digital controller/timer circuit 330. Similarly, ventricular depolarizations or R-waves in the LV-SENSE signal are sensed by a ventricular sense amplifier result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

Figure 6:
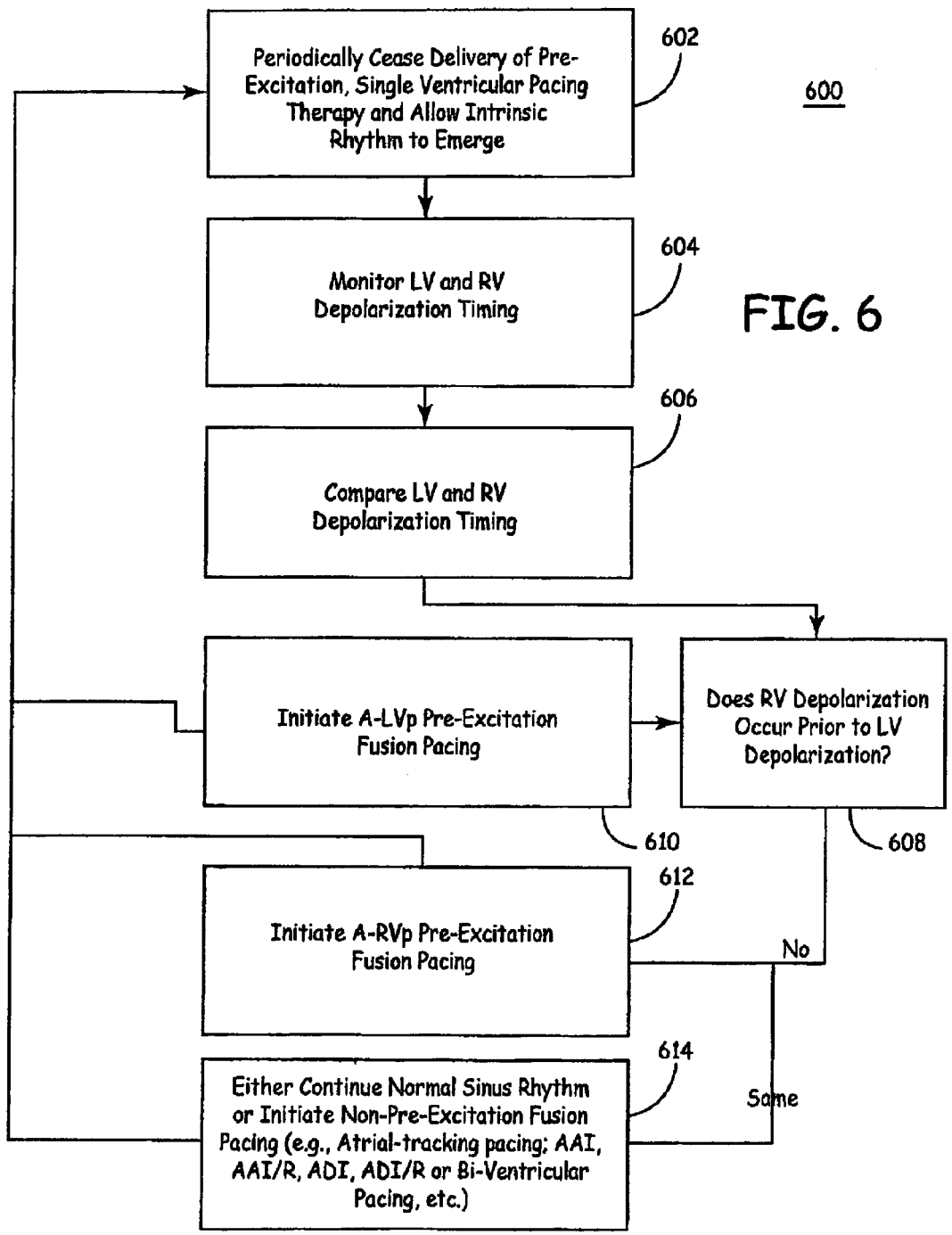
FIG. 6 depicts a process for periodically ceasing delivery of the pre-excitation, single ventricular pacing therapy to determine the cardiac conduction status of a patient and performing steps based on the status.

To simplify the description of FIGS. 4 through 6, it will be assumed that the following references to an "A-EVENT" and "A-PACE" will denote right atrial activity. In the event that the left atrium is monitored (or stimulated), the reader should appreciate that the LA is referred to.

Some of the operating modes of IPG circuit 300 according to the present invention are depicted in the flow charts (FIGS. 4–6) and described as follows. The particular operating mode of the present invention is a programmed or hard-wired sub-set of the possible operating modes as also described below. For convenience, the algorithm of FIGS. 4–6 is described in the context of determining the PEI delay and computing the A-V2p intervals to optimally pace the V2 chamber to produce electromechanical fusion with the corresponding intrinsic depolarization of the V1 chamber. The V1 chamber depolarizes intrinsically so that the pre-excited electromechanical fusion occurs as between the intrinsically activated V1 chamber and the pre-excitation evoked response of the V2 chamber. As noted below, the algorithm can be employed to determine an optimal PEI delay that results in an A-V2p interval producing ventricular synchrony (i.e., CRT delivery via a single ventricular pacing stimulus). Of course, the methods according to the present invention are intended to be stored as executable instructions on any appropriate computer readable medium although they may be performed manually as well.

FIG. 4 illustrates one embodiment of the present invention wherein the IPG circuit 300 includes a method 400 beginning with step S402 that is periodically performed to determine the intrinsic ventricular delay between the LV and the RV. In step 402 the first-to-depolarize ventricle is labeled V1 and the second-to-depolarize ventricle is labeled V2 and the corresponding shortest A-V interval is stored as the "A-V1" delay interval. In step 404 the A-V1 delay interval is decremented by the PEI to generate the A-V2p interval for delivering pacing stimulus to the V2 chamber. The magnitude of the PEI depends on several factors, including internal circuitry processing delay, location of sensing electrodes, location of pacing electrodes, heart rate, dynamic physiologic conduction status (e.g., due to ischemia, myocardial infarction, LBBB or RBBB, etc.). However, the inventors have found that a PEI of approximately 20–40 milliseconds (ms) oftentimes provides adequate pre-excitation to the V2 chamber resulting in electromechanical fusion of both ventricles. However, a reasonable range for the PEI runs from about one ms to about 100 ms (or more). Of course, an iterative subroutine for decrementing the A-V1 delay can be used and/or a clinical procedure utilized to help narrow a range of prospective values for the magnitude of the decrease in the A-V1 delay. According to this part of the present invention a series of decrements are implemented over a series of at least several cardiac cycles (as needed for the hemodynamic or contractile response to stabilize). The hemodynamic response can be gauged with external or internal sensors (e.g., surface ECG, intracardiac EGM, internal or endocardial pressure sensor, epicardial accelerometer, arterial flow sensor, etc.). Doppler echocardiography or ultrasound techniques may also be used to confirm the appropriate decrement of the A-V1 delay.

In another aspect, a data set is generated for a range of heart rates that correspond to measured A-V1 (and/or A-V2) delay intervals. The data may include paced or intrinsic heart rate data (ppm and bpm, respectively). In this aspect of the invention, the data set can be employed as a guiding or a controlling factor during heart rate excursions for continuous delivery of the single ventricular pre-excitation pacing of the present invention. In one form of this aspect of the invention, internal physiologic sensor data may be used as a guiding factor when determining an appropriate setting for the PEI (A-V2).

In yet another aspect, a first data set of appropriate values of the A-V2 delay interval are based on evoked response (i.e., wherein the A-EVENT is a pacing event) and a second data set of appropriate values of the A-V2 delay interval are based on intrinsic response (i.e., wherein the A-EVENT is a natural atrial depolarization).

Following the decrementing step 404 the A-V2p (pacing) delay interval is set and in step 406 pre-excitation pacing therapy is delivered to the V2 chamber upon expiration of the A-V1p interval.

In the presently illustrated embodiment of the invention, pre-excitation pacing therapy delivery continues until: a pre-set number of cardiac cycles occur, a pre-set time period expires, a loss of capture occurs in the V2 chamber, or a physiologic response trigger event occurs. The physiologic response trigger will be described below. With respect to the other three situations, the number of cardiac cycles or the time period may be set to any clinically appropriate value, given the patient's physiologic condition (among other factors) before returning to step 402 and (re-)determining the physiologic A-V1 interval and deriving an operating PEI (A-V2p). If a loss of capture in the V2 chamber is detected it could indicate that the V2p (pacing) stimulus is being delivered too late (e.g., during the refractory period of the V2 chamber) or that the V2 pacing electrodes have malfunctioned or become dislodged. While the process 400 depicted in FIG. 4 reflect that under all the foregoing situations steps 402–406 should be performed following events (i)–(iii), the pre-excitation pacing therapy could of course be discontinued or a mode switch could be performed to another pacing modality (e.g., an AAI, ADI, AAI/R, ADI/R, double chamber DDD or DDD/R, and the like).

With respect to the physiologic response trigger event(s)—as well as optionally with respect to condition (iii) wherein loss of capture of the V2 chamber occurs due to inappropriate timing of the V2 pacing stimulus—at step 410 an iterative closed-loop process for determining an appropriate A-V2p interval is performed. In step 410, the A-V2p interval is directly manipulated from a prior operating value while one or more physiologic response is monitored and/or measured and stored. As mentioned above with respect to step 404 with regard to decrementing the intrinsic A-V1 interval to generate the operating A-V2p interval, a number of sensors may be employed. After storing the physiologic response data (and corresponding PEI used during data collection) at step 412 the data is compared and the PEI corresponding to the most favorable physiologic response is then programmed as the operating PEI. The process then proceeds back to step 406 and the V2 chamber receives pre-excitation pacing therapy upon the expiration of the physiologically-derived PEI. Of course, of the foregoing steps, steps 402,404,406 may be performed wherein step 402 (deriving the PEI from A-V1 interval) is only performed occasionally (e.g., every ten cardiac cycles, during heart rate excursions, etc.). In this form of the invention, the magnitude of the decrement of the A-V1, or the PEI itself, can be based upon one or more prior operating PEI value (and several prior operating PEI values, with the most recent PEI receiving additional statistical weighting). In addition to or in lieu of the foregoing a look up table (LUT) or other data compilation, as described above, may be utilized to guide or control the derivation of the PEI value (as described in more detail with respect to FIG. 5).

Now turning to FIG. 5, another embodiment of a method according to the present invention is depicted as process 500. To begin process 500, the steps 502,504,506,508 correspond closely to the corresponding steps of process 400 (FIG. 4) just described. However, at step 510—in the event that condition (iv) of step 508 is declared—a data set (or LUT) of physiologic responses and corresponding PEI values for a given patient is accessed. At step 512 the PEI is programmed to a value corresponding to the current physiologic response trigger for the patient. Then, at step 506, pre-excitation pacing ensues upon expiration of the newly programmed PEI. A representative physiologic response trigger includes an upward or downward heart rate excursion, a sensed lack of ventricular synchrony (based on accelerometer, pressure, EGM or other physiologic data signals) and the like.

In FIG. 6, a process 600 for periodically ceasing delivery of the pre-excitation, single ventricular pacing therapy to perform a pacing mode switch to a different form of pre-excitation therapy, ceasing pre-excitation therapy, or allowing normal sinus rhythm to continue (chronically) is illustrated. The process 600 can be implemented as a part of steps 402,502 (or process 400 and 500, respectively) for determining the intrinsic A-V1 interval or can be performed independently. In either case, process 600 is designed to help reveal improvement (or decline) of a patient's condition. In the former case, if so-called "reverse remodeling" of the myocardium occurs resulting in return of ventricular synchrony and improved hemodynamics and autonomic tone, pre-excitation therapy delivery may be temporarily or permanently terminated. The patient may, in the best scenario, be relieved of pacing therapy delivery altogether (programming the pacing circuitry to an ODO monitoring-only "pacing modality"). Assuming the patient is not chronotropically incompetent, normal sinus rhythm may emerge permanently for all the activities of daily living. Additionally, the process 600 may be employed to search for a change in conduction status (e.g., wherein V2 changes from LV to RV, or wherein A-V1 conduction timing changes, etc.). According to process 600, at step 602 the delivery of pre-excitation therapy ceases and for at least one cardiac cycle the intrinsic, normal sinus rhythm is allowed to emerge. At step 604 the depolarization(s) of the LV and RV are monitored (and, optionally stored in memory). At step 606 a comparison of the depolarization timing is compared and at decision step 608 three outcomes are determined based on the comparison of depolarization timing. If the RV depolarization occurs prior to the LV depolarization then step 610 is performed wherein the LV comprises the V2 chamber and A-LVp pre-excitation is initiated (according to process 400 or 500 or analogues thereof). However, if the LV depolarization occurs prior to the RV depolarization then step 612 is performed wherein the RV comprises the V2 chamber and A-RVP pre-excitation is initiated (according to process 400 or 500 or analogues thereof). Finally, if the RV depolarization occurs substantially at the same time as the LV depolarization then step 614 is performed. In step 614, either normal sinus rhythm is allowed to continue or a non-pre-excitation pacing therapy is initiated. Some examples of such therapy include: AAI, AAI/R, ADI, ADI/R, double chamber DDD, DDD/R and bi-ventricular pacing, and the like.

In addition to or in lieu of the subject matter described above (in particular with respect to FIG. 5 and FIG. 6), fusion pacing can be suspended for one or more cardiac cycles while V1 depolarization(s) are monitored. Also, a form of CRT delivery could be implemented wherein the V2 pacing therapy delivery is triggered off a sensed (intrinsic) depolarization of the V1 chamber. The latter technique allows collection of intrinsic A-V1 timing while still preserving some of the hemodynamic benefit of CRT delivery. In addition, the intra-ventricular conduction time (IVCT) can be measured and used to assist calculate appropriate timing according to the invention. The IVCT could be measured between a (relatively early) pacing stimulus delivered to the V1 chamber and sensing the conduction time until the V2 chamber depolarizes (and vice versa). Furthermore, since the electrodes disposed in the V1 chamber are primarily, if not exclusively, only sensing intrinsic ventricular activity said electrodes can be programmed with very short blanking periods and thus used to measure so-called "far-field" R-waves from the V2 chamber.

It should be understood that, certain of the above-described structures, functions and operations of the pacing systems of the illustrated embodiments are not necessary to practice the present invention and are included in the description simply for completeness of an exemplary embodiment or embodiments. It will also be understood that there may be other structures, functions and operations ancillary to the typical operation of an implantable pulse generator that are not disclosed and are not necessary to the practice of the present invention.

In addition, it will be understood that specifically described structures, functions and operations set forth in the above-referenced patents can be practiced in conjunction with the present invention, but they are not essential to its practice. It is therefore to be understood, that within the scope of the appended claims, the invention may be practiced otherwise than as specifically described without actually departing from the spirit and scope of the present invention.

The invention claimed is:

1. A method of bi-ventricular, fusion-pacing therapy delivery to a non-synchronous pair of ventricles, including delivery of a single ventricular pre-excitation pacing pulse to a relatively late activated ventricular chamber to promote mechanical synchrony between the late activated ventricular chamber and a relatively more rapid, intrinsically conducting ventricular chamber, comprising:
   measuring an intrinsic atrio-ventricular delay interval for a first-to-depolarize ventricular (V1) chamber for at least two prior cardiac cycles; and
   delivering during a subsequent cardiac cycle at least one ventricular pre-excitation pacing pulse to a second-to-depolarize ventricular (V2) chamber,
wherein said at least one ventricular pre-excitation pacing pulse is delivered at the expiration of a V2 pacing interval, wherein the V2 pacing interval is temporally shorter than an A-V1 delay interval derived from the measured intrinsic atrio-ventricular delay intervals of the V1 chamber.

2. A method according to claim 1, wherein the step of measuring the intrinsic atrio-ventricular (AV) delay interval further comprises at least one of:
   calculating an average AV delay interval,
   calculating a weighted average AV delay,
   calculating a median AV delay interval,
   looking up an AV delay interval correlated to a heart rate,
   looking up an AV delay interval correlated to an activity sensor input,
   looking up an AV delay interval correlated to a minute respiration value,
   looking up an AV delay interval correlated to a fluid pressure signal,
   looking up an AV delay interval correlated to an acceleration signal.

3. A method according to claim 1, wherein the first-to-depolarize ventricular chamber (V1) comprises a right ventricle.

4. A method according to claim 1, wherein said at least one ventricular pre-excitation pacing pulse is delivered via at least one electrode adapted to be coupled to a left ventricular chamber.

5. A method according to claim 4, wherein the step of delivering a pre-excitation pulse to said at least on electrode in the left ventricular chamber comprises the pulse to a portion of one of:
   a coronary sinus,
   a portion of a great vein,
   a portion of a vessel branching from the great vein.

6. A method according to claim 1, wherein said at least one ventricular pre-excitation pacing pulse is delivered between a tip and a ring pacing electrode, a pair of electrodes, a coil and a can-based electrode, a pair of coil electrodes, an epicardial electrode and a second electrode, or a subcutaneous electrode and the second electrode.

7. A method according to claim 1, wherein the measuring step occurs between at least one of:
a tip and a ring pacing electrode,
a pair of electrodes,
a coil and a can-based electrode.
a pair of coil electrodes,
an epicardial electrode and a second electrode,
a subcutaneous electrode and the second electrode.

8. A method according to claim 7, wherein at least one of said electrode(s) is adapted to couple to an anterior portion of the left ventricle.

9. A method according to claim 1, wherein said at least one ventricular pre-excitation pacing pulse is delivered with at least one electrode adapted to couple epicardially to the V2 chamber.

10. A method according to claim 1, wherein the subsequent cardiac cycle comprises an immediately subsequent cardiac cycle.

11. A method according to claim 1, wherein the at least two prior cardiac cycles comprises three or more cardiac cycles.

12. A method according to claim 1, wherein the at least two prior cardiac cycles comprise at least three prior cardiac cycles.

13. A method according to claim 12, wherein the most recent of the at least three prior cardiac cycles are mathematically weighted more heavily than the other said cardiac cycles.

14. A method according to claim 1, further comprising;
monitoring a physiologic cardiac parameter of a patient during delivery of the fusion-based cardiac pacing regimen.

15. A method according to claim 14, further comprising:
comparing the physiologic parameter to a threshold value; and
based on the results of the comparison, performing one of:
a. ceasing delivery of the fusion-based cardiac pacing regimen,
b. applying a bi-ventricular pacing regimen on a beat-by-beat basis,
c. decrementing the V2 interval.

16. A method according to claim 11, wherein the pre-excitation interval comprises a discrete interval of a plurality of discrete intervals and said plurality of intervals are correlated to an output signal that is in turn correlated to a physiologic parameter, and further comprising:
monitoring the output signal; and
delivering at least one ventricular pre-excitation pacing pulse at the expiration of the discrete interval.

17. A method according to claim 16, wherein the output signal comprises at least one of: a heart rate output signal, a cardiac pressure output signal, a minute ventilation output signal, an activity sensor output signal, an acceleration output signal.

18. A method according to claim 17, wherein the plurality of discrete intervals are stored as a data set and wherein each discrete interval of the data set corresponds to a magnitude of the output signal.

19. An apparatus for delivering bi-ventricular, fusion-pacing therapy to one of a non-synchronous pair of ventricles, to promote mechanical synchrony between an intrinsically first-to-depolarize ventricular chamber and an intrinsically second-to-depolarize, ventricular chamber, comprising:
means for measuring an intrinsic atrio-ventricular delay interval for a first-to-depolarize ventricular (V1) chamber for at least two prior cardiac cycles; and
means for delivering during a subsequent cardiac cycle at least one ventricular pre-excitation pacing pulse to a second-to-depolarize ventricular (V2) chamber, wherein said at least one ventricular pre-excitation pacing pulse is delivered at the expiration of a V2 pacing interval, wherein the V2 pacing interval is temporally shorter than an A-V1 delay interval derived from the measured intrinsic atrio-ventricular delay intervals of the V1 chamber.

20. An apparatus according to claim 19, wherein the means for measuring the intrinsic atrio-ventricular (AV) delay interval further comprises at least one of the following:
means for calculating an average AV delay interval,
means for calculating a median AV delay interval,
means for calculating a weighted average AV delay,
means for measuring a prior intrinsic AV delay interval,
means for looking up an AV delay interval correlated to a heart rate,
means for looking up an AV delay interval correlated to an activity sensor input,
means for looking up an AV delay interval correlated to a minute respiration value,
means for looking up an AV delay interval correlated to a fluid pressure signal,
means for looking up an AV delay interval correlated to an acceleration signal.

21. An apparatus according to claim 19, wherein the V1 chamber comprises a right ventricle.

22. An apparatus according to claim 19, wherein said at least one ventricular pre-excitation pacing pulse is delivered via at least one electrode adapted to be coupled to a left ventricular chamber, which comprises the V2 chamber.

23. An apparatus according to claim 22, wherein the at least one electrode is adapted to couple to a portion of one of:
a coronary sin us,
a portion of a great vein,
a portion of a vessel branching from the great vein.

24. An apparatus according to claim 19, wherein said at least one ventricular pre-excitation pacing pulse is delivered between:
a tip and a ring pacing electrode, a pair of electrodes, a coil and a can-based electrode, a pair of coil electrodes, an epicardial electrode and a second electrode, or a subcutaneous electrode and the second electrode.

25. An apparatus according to claim 19, wherein the means for measuring comprises at least one of:
a tip and a ring pacing electrode,
a pair of electrodes,
a coil and a can-based electrode,
a pair of coil electrodes,
an epicardial electrode and a second electrode,
a subcutaneous electrode and the second electrode.

26. An apparatus according to claim 25, wherein at least one of said electrode(s) is adapted to couple to an anterior portion of the left ventricle.

27. An apparatus according to claim 19, wherein said at least one ventricular pre-excitation pacing pulse is delivered with at least one electrode adapted to couple epicardially to the second-to-depolarize ventricular chamber.

28. An apparatus according to claim 19, wherein the subsequent cardiac cycle comprises an immediately subsequent cardiac cycle.

29. An apparatus according to claim 19, wherein the at least one prior cardiac cycle comprises an immediately prior cardiac cycle.

30. An apparatus according to claim 19, wherein the at least two prior cardiac cycles comprise at least three prior cardiac cycles.

31. An apparatus according to claim 30, wherein the most recent of the at least three prior cardiac cycles is mathematically weighted more heavily than the other said cardiac cycles.

32. An apparatus according to claim 19, further comprising:
means for monitoring a physiologic cardiac parameter of a patient during delivery of the fusion-based cardiac pacing regimen.

33. An apparatus according to claim 32, further comprising:
means for comparing the physiologic parameter to a threshold value; and at least one of:
a. means for ceasing delivery of the fusion-based cardiac pacing regimen,
b. means for applying a bi-ventricular pacing regimen on a beat-by-beat basis,
c. means for decrementing the V2 pacing interval.

34. An apparatus according to claim 29, wherein the pre-excitation interval comprises a discrete interval among a plurality of discrete intervals and said plurality of intervals are correlated to a heart rate, and further comprising:
means for monitoring the heart rate of a patient; and
means for delivering at least one ventricular pre-excitation pacing pulse at the expiration of the discrete interval.

35. An apparatus according to claim 34, wherein the heart rate comprises a range of heart rates.

36. An apparatus according to claim 35, wherein the plurality of discrete intervals are stored as a data set and wherein each discrete interval corresponds to a range of heart rates.

37. A computer readable medium for storing instructions for delivering bi-ventricular, fusion-pacing therapy to one of a non-synchronous pair of ventricles, to promote mechanical synchrony between an intrinsically first-to-depolarize ventricular chamber and an intrinsically second-to-depolarize, ventricular chamber, comprising:
instructions for measuring an intrinsic atrio-ventricular delay interval for a first-to-depolarize ventricular (V1) chamber for at least two prior cardiac cycles; and
instructions for delivering during a subsequent cardiac cycle at least one ventricular pre-excitation pacing pulse to a second-to-depolarize ventricular (V2) chamber, wherein said at least one ventricular pre-excitation pacing pulse is delivered at the expiration of a V2 pacing interval, wherein the V2 pacing interval is temporally shorter than an A-V1 delay interval derived from the measured intrinsic atrio-ventricular delay intervals of the V1 chamber.

38. A medium according to claim 37, wherein the instructions for measuring the intrinsic atrio-ventricular (AV) delay interval further comprises at least one of the following:
instructions for calculating an average AV delay interval,
instructions for calculating a weighted average AV delay interval,
instructions for calculating a median AV delay interval,
instructions for measuring a prior intrinsic AV delay interval,
instructions for looking up an AV delay interval correlated to a heart rate,
instructions for looking up an AV delay interval correlated to an activity sensor input,
instructions for looking up an AV delay interval correlated to a minute respiration value,
instructions for looking up an AV delay interval correlated to a fluid pressure signal,
instructions for looking up an AV delay interval correlated to an acceleration signal.

39. A medium according to claim 37, wherein the V1 chamber comprises a right ventricle.

40. A medium according to claim 37, wherein said at least one ventricular pre-excitation pacing pulse is delivered via at least one electrode adapted to be coupled to a left ventricular chamber.

41. A medium according to claim 40, wherein the at least one electrode is adapted couple to a portion of one of:
a coronary sinus,
a portion of a great vein,
a portion of a vessel branching from the great vein.

42. A medium according to claim 37, wherein said at least one ventricular pre-excitation pacing pulse is delivered between:
a tip and a ring pacing electrode, a pair of electrodes, a coil and a can-based electrode, a pair of coil electrodes, an epicardial electrode and a second electrode, or a subcutaneous electrode and the second electrode.

43. A medium according to claim 37, wherein the instructions for measuring comprises at least one of;
a tip and a ring pacing electrode.
a pair of electrodes,
a coil and a can-based electrode,
a pair of coil electrodes,
an epicardial electrode and a second electrode,
a subcutaneous electrode and the second electrode.

44. A medium according to claim 43, wherein at least one of said electrode(s) is adapted to couple to an anterior portion of the left ventricle.

45. A medium according to claim 37, wherein said at least one ventricular pre-excitation pacing pulse is delivered with at least one electrode adapted to couple epicardially to the V2 chamber.

46. A medium according to claim 37, wherein the subsequent cardiac cycle comprises an immediately subsequent cardiac cycle.

47. A medium according to claim 37, wherein the at least two prior cardiac cycles comprise two immediately prior cardiac cycles.

48. A medium according to claim 37, wherein the at least two prior cardiac cycles comprise at least three prior cardiac cycles.

49. A medium according to claim 48, wherein the most recent of the at least three consecutive, immediately prior, cardiac cycles is mathematically weighted more heavily than the other said cardiac cycles.

50. A medium according to claim 37, further comprising:
instructions for monitoring a physiologic cardiac parameter of a patient during delivery of the bi-ventricular, fusion-pacing therapy.

51. A medium according to claim 50, further comprising:
instructions for comparing the physiologic parameter to a threshold value; and at least one of:
a. instructions for ceasing delivery of the bi-ventricular fusion-pacing therapy,
b. instructions for applying the bi-ventricular fusion-pacing therapy on a beat-by-beat basis,
c. instructions for decrementing the V2 pacing interval.

* * * * *

UNITED STATES PATENT AND TRADEMARK OFFICE
CERTIFICATE OF CORRECTION

| | | |
|---|---|---|
| PATENT NO. | : 7,181,284 B2 | Page 1 of 1 |
| APPLICATION NO. | : 10/803570 | |
| DATED | : February 20, 2007 | |
| INVENTOR(S) | : Burnes et al. | |

It is certified that error appears in the above-identified patent and that said Letters Patent is hereby corrected as shown below:

In column 18, line 37 please change "a coronary sin us" to --a coronary sinus--.

Signed and Sealed this

Thirtieth Day of October, 2007

JON W. DUDAS
*Director of the United States Patent and Trademark Office*